United States Patent [19]

Eikmeyer

[11] Patent Number: 4,634,281
[45] Date of Patent: Jan. 6, 1987

[54] APPARATUS FOR THE INSPECTION OF CONTINUOUS SHEETS OF MATERIAL

[75] Inventor: Peter Eikmeyer, Bielefeld, Fed. Rep. of Germany

[73] Assignee: Feldmuehle Aktiengesellschaft, Dusseldorf, Fed. Rep. of Germany

[21] Appl. No.: 664,154

[22] Filed: Oct. 24, 1984

[30] Foreign Application Priority Data

Oct. 26, 1983 [DE] Fed. Rep. of Germany ....... 3338802

[51] Int. Cl.$^4$ .................... G01N 21/89; G01N 21/86
[52] U.S. Cl. .................................. 356/431; 250/563; 356/239
[58] Field of Search ............... 356/239, 431; 250/563, 250/572

[56] References Cited

U.S. PATENT DOCUMENTS 3,609,380 9/1971 Shaw .................................. 356/239
4,306,808 12/1981 Vander Neut ...................... 356/239

FOREIGN PATENT DOCUMENTS

1507548 4/1978 United Kingdom .

Primary Examiner—R. A. Rosenberger
Attorney, Agent, or Firm—Felfe & Lynch

[57] ABSTRACT

The inspection for surface deformation of flat glass is carried out by the flying-spot method wherein the beam of light is thrown by a rotating mirror 13 onto a folding mirror 6 which reflects the light onto the continuous sheet of glass 2 to be inspected. The reflected light beam 4 strikes a light-diffusing plate 1 disposed ahead of the receiver 11. The area of the light-diffusing plate 1 on which the beam of light impinges when the sheet of glass 2 is free of defects is opaque. On this opaque area there are disposed in a spaced relationship two photodiodes 7 between which a light bar formed by the scanning light beam extends. When the thickness of the flat glass 2 varies gradually, light will strike one of the photodiodes 7. The pulse so triggered controls a tracking mechanism 50 which adjusts the folding mirror 6 so that the light bar again extends between the photodiodes 7.

9 Claims, 8 Drawing Figures

Fig. 6

APPARATUS FOR THE INSPECTION OF CONTINUOUS SHEETS OF MATERIAL

This invention relates to an apparatus for the inspection of continuous sheets of a light-transmissive material, for example, transparent flat glass or the like, which may have defects such as transparent surface deformations and/or inclusions. The apparatus preferably comprises a light source, and, more particularly, a laser, a rotating mirror associated therewith for generation of a beam of light onto a mirror which reflects the light beam onto the sheet of material, and at least one receiver for the transmitted light comprising a housing covered with a light-diffusing plate and in which at least one photoelectric transducer is disposed.

An apparatus of this type is described in published German patent application DOS No. 24 11 407, this apparatus being used especially to inspect flat glass. The present invention, therefore, will be described also in terms of flat-glass inspection without, however, being limited thereto.

In the inspection of flat glass, defect detection as such is not particularly critical. However, one problem arises which cannot readily be solved.

Deformations of the surface or also of the underside of continuous sheets of flat glass are usually limited to relatively small areas. These deformations will immediately trigger a defect indication, which is what is desired. However, a gradual, steady thickness variation also influences the measurements, although in such a case the thickness variation can usually be tolerated.

The inspection itself is usually carried out by scanning the surface of the flat glass with a light beam, which usually is a laser beam, at right angles to the direction of travel of the continuous sheet of glass. A narrow optical receiver beneath the glass picks up the light passing through the glass. The receiver is covered with a diffuser, preferably with a light-diffusing plate, usually in the form of a ground glass, or with an appropriately colored film that is disposed between two clear glass plates, so that the light beam striking the diffuser is transformed into diffuse light and picked up by the optical receiver.

The light beam itself preferably is generated by a laser, generally a helium-neon laser, and thrown onto a rotating mirror which projects it onto a fixed mirror in the inspection apparatus serving to fold the beam path and known as a folding mirror, which then reflects this beam of light onto the continuous sheet of glass to be inspected.

As the light enters the glass and exits from it, the light beam is refracted. The thickness of the glass and the angle of incidence of the light beam determine the position of the transmitted light beam imaged on the diffuser; in other words, in the case of a thickness variation, the light beam may fall outside a stop on the transparent area of the diffuser and thus result in a defect indication even though only a tolerable steady variation of glass thickness without inclusions may be present.

SUMMARY OF THE INVENTION

An object of the invention is to carry out an inspection of the glass which is not influenced by any thickness variations which may be present in the glass.

In an apparatus of the type outlined, this object preferably is accomplished by the following characteristics in combination:

(a) The area of the light-diffusing plate on which the light beam falls which is reflected or transmitted when the continuous sheet is free of defects is opaque.

(b) Two photodiodes staggered relative to each other in the direction of travel of the continuous sheet are disposed on the opaque area.

(c) The folding mirror is pivotally mounted.

(d) The folding mirror is provided with a tracking mechanism.

(e) The photodiodes are connected to the tracking mechanism through a control unit.

The diffuser of the receiver, preferably the light-diffusing plate ahead of the receiver, preferably is provided in its center with a so-called stop. A stop preferably is either an opaque coloration of the diffuser or an opaque cover which prevents the direct light beam from entering the receiver so that no light reaches the receiver when there are no defects in the glass. Only when it is deflected by a surface-deforming defect does the light impinge on the transparent areas of the diffuser and so reach the receiver, thus resulting in unambiguous defect signals. The position of the stop on the diffuser is determined by the thickness of the material as a function of the angle of impingement of the scanning light beam. It preferably is adjustable. The requisite width of the stop preferably is essentially determined by the diameter of the scanning light spot and by minor variations in the scanning motion which are within the tolerances of the rotating-mirror system.

To prevent erroneous defect indications which are due, not to a sudden deflection of the light beam by surface deformations but to a gradual, steady thickness increase or decrease of the continuous sheet, and hence to a drifting of the light bar imaged on the stop in the direction of travel or in the opposite direction, there preferably are disposed on the opaque area of the diffuser, in other words, directly on the stopper, two photodiodes located at the longitudinal edges of the stopper so that they are spaced apart by practically the entire width of the stop. The light bar passing through the sheet preferably should extend practically as the axis of symmetry between these two points on the stop. This will be the case (a) when no defect is present in the continuous sheet, and (b) when there is no thickness variation.

When a defect is present and the scanning beam strikes that defect, there occurs a momentary deflection of the beam during a scanning motion; in other words, the scanning spot, which due to rapid motion appears as a light bar on the stop, locally leaves the area of the stop momentarily and reaches the transparent area of the diffuser. This triggers a defect signal.

In contrast to this momentary local deflection of the scanning beam in the presence of defects, deflection of the beam due to a thickness variation of the continuous glass sheet occurs slowly and over the entire width. This manifests itself in that upon repeated scanning the scanning beam slowly drifts either into the right or the left photodiode, depending on the sign of the thickness variation, the word "slowly" being referred to the scanning rate and to the rate of advance of the continuous sheet of glass to be inspected, for example, to a period of about one second. When light falls on one of the photodiodes, a control pulse is triggered which acts upon the tracking mechanism, advantageously through a positive-negative controller in a three-level action closed loop, thus re-positioning the pivotally mounted folding mirror so that the scanning line again extends midway between the two photodiodes. Adjustment of the reflecting mirror thus occurs automatically with varying thickness of the material.

In an advantageous embodiment of the invention, the tracking mechanism comprises an electric motor with an extremely geared-down transmission that is coupled to the pivotally mounted mirror and adjusts it on the basis of the commands triggered by the photodiodes. Since a strict yes/no interpretation of the signals ordinarily will not result in satisfactory operation of the automatic tracking mechanism, the amplitudes of the signals from the photodiodes are evaluated, for example, fed through an amplifier to a control circuit which transmits the control pulses derived therefrom to the electric motor.

In a preferred embodiment of the invention, the diffuser ahead of the receiver is covered in the area of the transmitted beam with an opaque plate as a stop. A regular transparent plate can be provided with an opaque area just by using an opaque sheet, which in the simplest case may be a strip of black adhesive tape applied to the transparent plate of the receiver. However, a metal sheet which like the black adhesive tape has a certain width might also be used as a stop.

In accordance with the invention, apparatus for the inspection of a continuous sheet of a light-transmissive material which may have defects comprises a light source for supplying a light beam and first movable mirror means associated therewith for directing a beam of light to second movable mirror means for reflecting the light beam onto the sheet of material to be inspected. The apparatus also includes receiver means for receiving the reflected light comprising a plurality of light-responsive transducer means and a housing including light-diffusing means, the reflected light beam falling on an area of the light-diffusing means and the aforesaid area being opaque when the continuous sheet of material is free of defects. At least two of the light-responsive transducer means are spaced relative to each other in the direction of travel of the continuous sheet of material. The apparatus also includes control means responsive to the transducer means for re-positioning the second mirror means in response to gradual thickness changes of the light-transmissive material.

For a better understanding of the present invention, together with other and further objects thereof, reference is made to the following description, taken in connection with the accompanying drawings, and its scope will be pointed out in the appended claims.

Referring now to the drawings.

Figure 1:
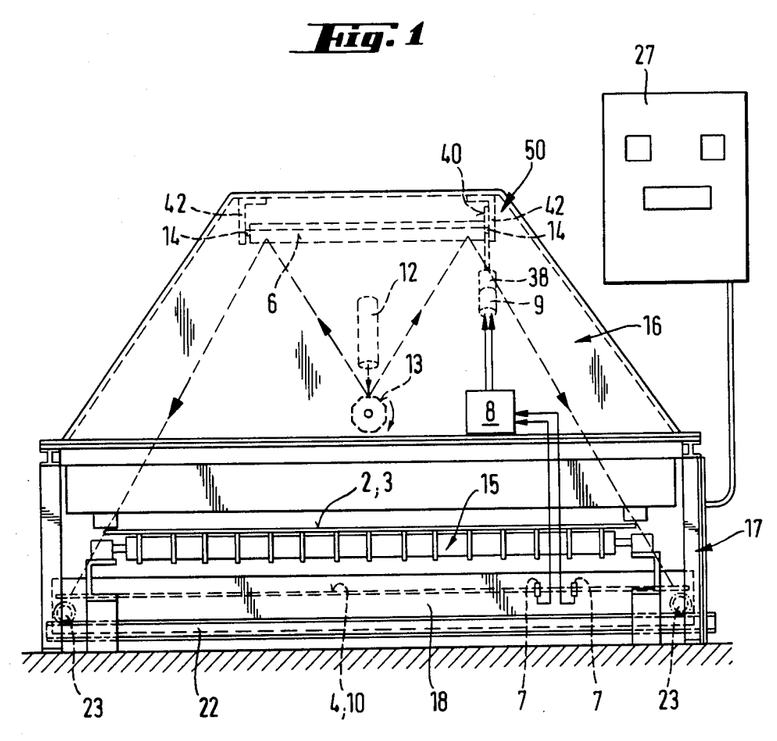
FIG. 1 is a diagrammatic fragmentary, sectional view in front elevation of an inspection apparatus for transparent materials.

Referring now to FIG. 1, a laser head 12 throws a light beam onto a rotating mirror 13 which directs the light beam to a folding mirror 6. The folding mirror 6 preferably is pivotally supported in bearings 14 and can be adjusted by an electric motor 9 through reduction gearing 38.

Figures 2A, 2B:
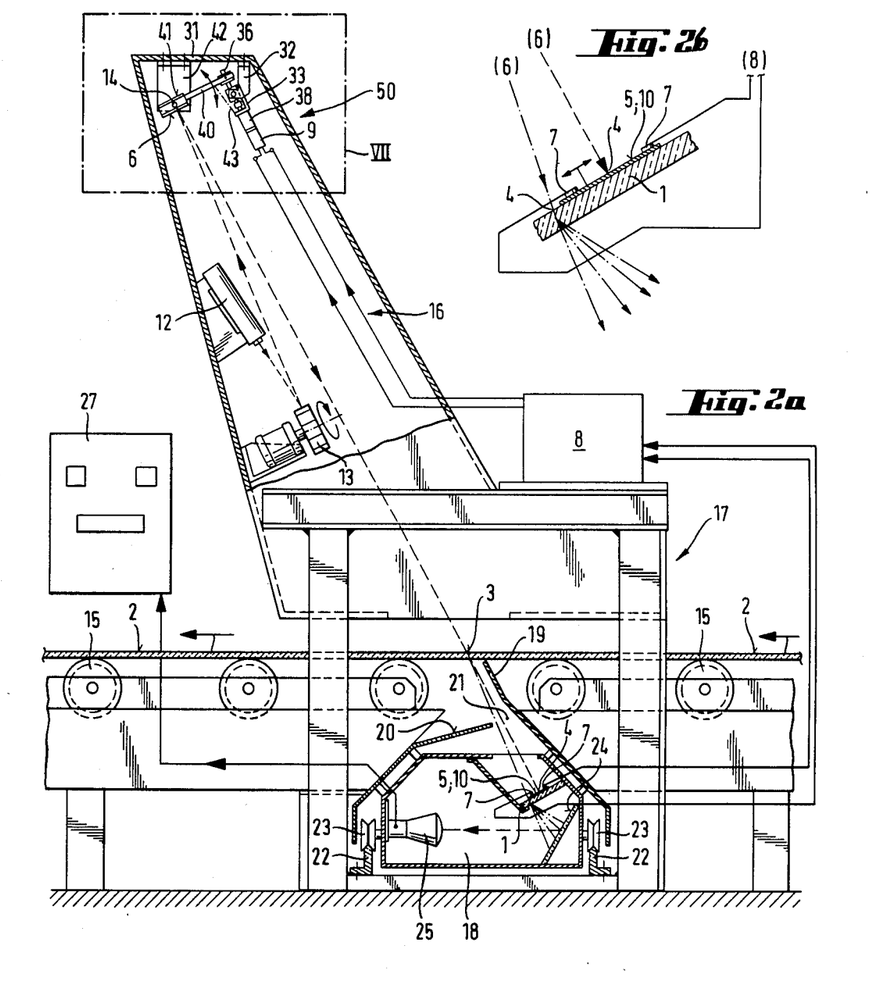
FIG. 2a represents diagrammatically the same apparatus in a fragmentary, sectional view in side elevation.
FIG. 2b represents diagrammatically an enlargement of a portion of the FIG. 2a apparatus.

In the present embodiment, the continuous sheet of material 2 to be inspected is a glass sheet which is conveyed on rollers 15 through the inspection apparatus in the direction of the arrow (FIG. 2a).

Figure 3:
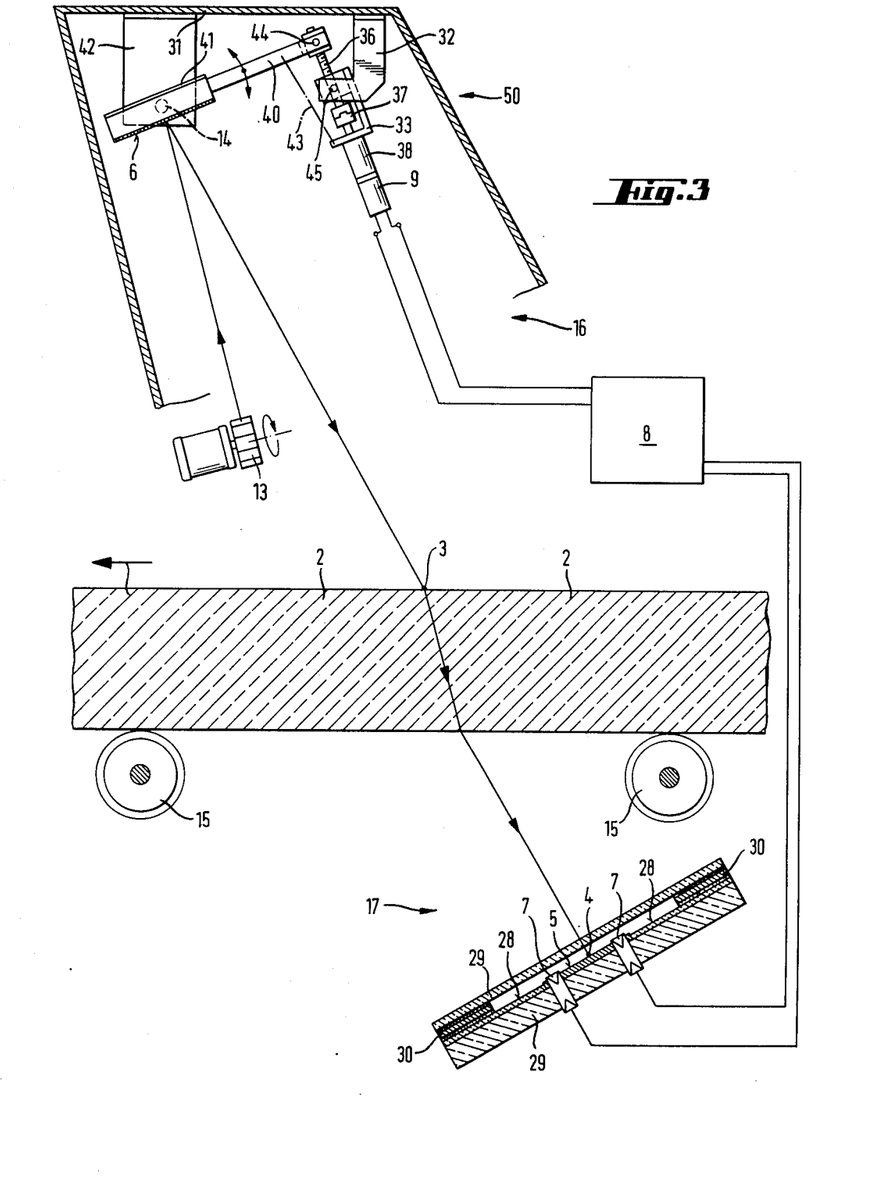
FIG. 3 represents diagrammatically, in enlarged detail, the path of the scanning beam in the inspection for light transmission of thick continuous sheets of a transparent material.

The entire inspection apparatus preferably is divided into two sections, the transmitting section 16 and the receiving section 17. The latter comprises a housing 18 which comprises a fragment rejector 19 that forms with a housing cover 20 a gap 21 for the entry of a light beam 3 reflected by the folding mirror 6 onto the sheet of material 2. When the sheet of material 2 is free of defects, this reflected light beam 3 preferably is imaged as a transmitted light bar 4 on a stop 5 disposed on a light-diffusing plate 1 (FIG. 2b) or between two light-diffusing strips of film 28 (FIG. 3). In the embodiment with light-diffusing strips of film 28, the latter are mounted between two plates 29 made of flawless glass which, as shown in FIG. 3, further accommodates an aperture boundary plate 30 in the marginal region. Photodiodes 7 preferably penetrate the lower glass plate 29 and the stopper 5.

Figure 4:
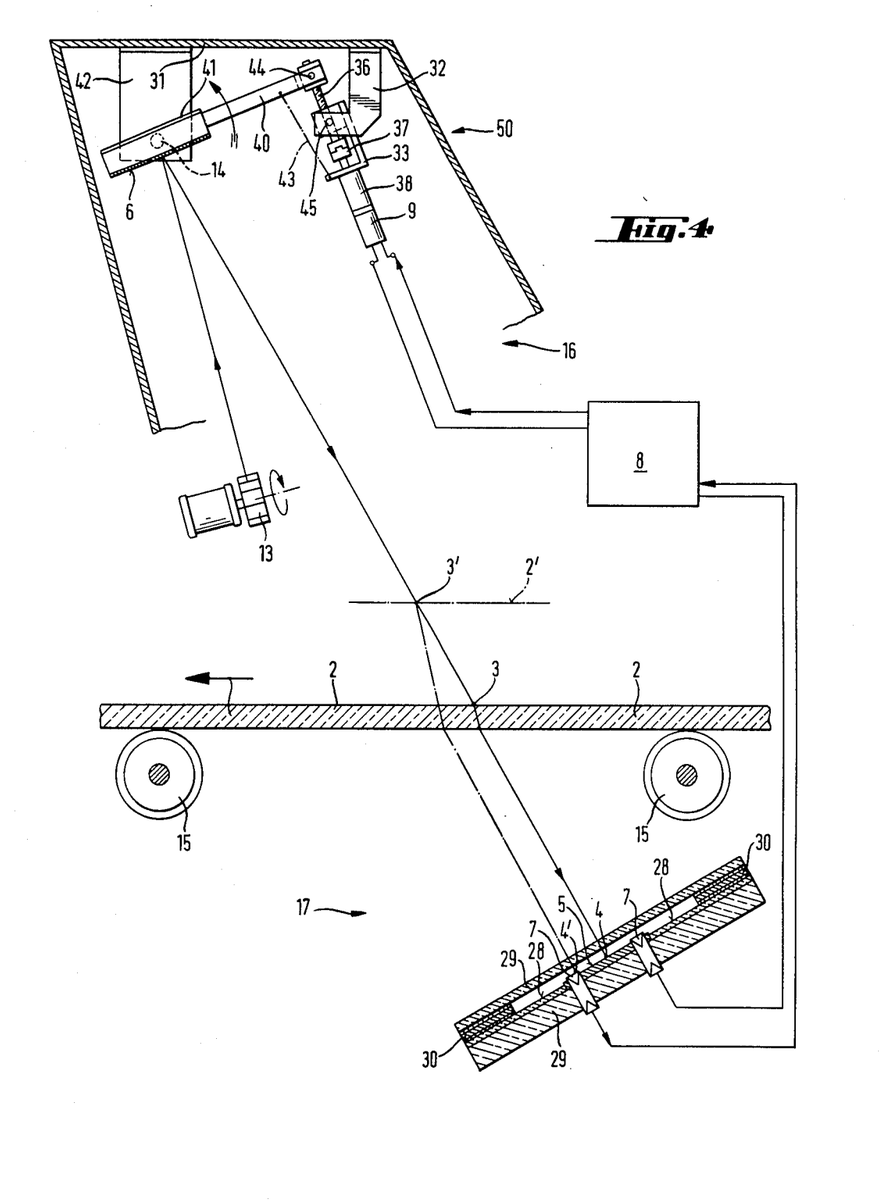
FIG. 4 represents diagrammatically, in enlarged detail, the scanning beam path in the case of thin continuous sheets of a transparent material.
Figure 5:
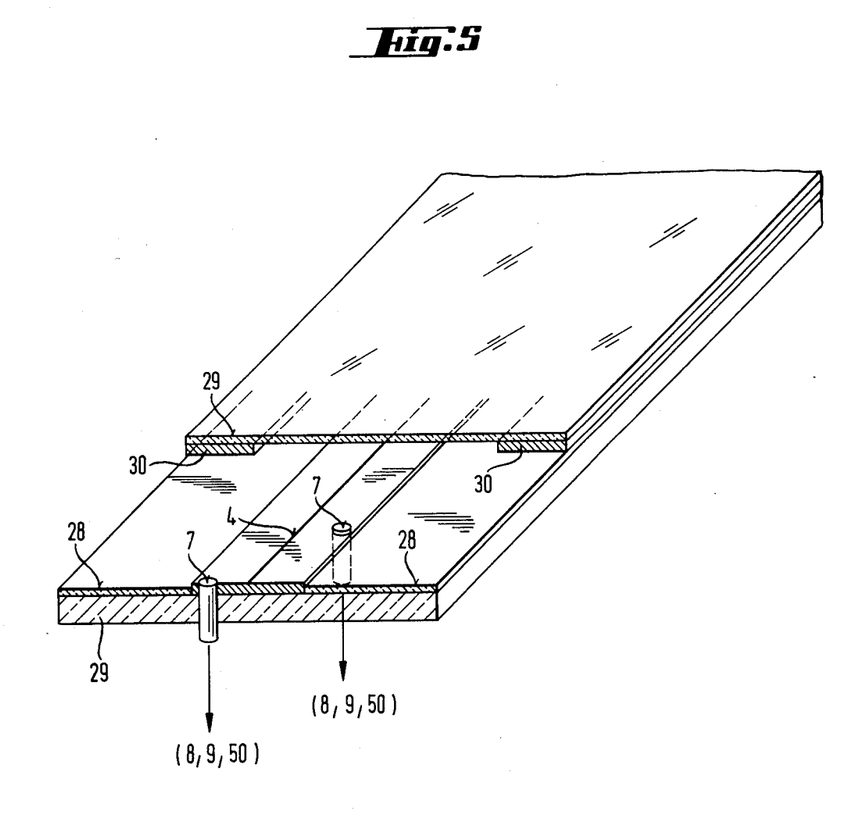
FIG. 5 represents diagrammatically, to an enlarged scale, the arrangement of the photodiodes on the light-diffusing plate of the receiver.

The stop 5 preferably carries two photodiodes 7 located in proximity to its right and left edges. When the sheet of material 2 is free of defects, the transmitted light bar 4 falls practically on the center of the stop 5 and thus comes to lie between the two photodiodes 7. Now when a variation in the thickness of the sheet of material 2 causes a shift in the scanning line, the light bar 3 will be displaced on the sheet of material 2. The transmitted light bar 4 then enters the housing 18 in a different position, in other words, shifts its position on the stop 5 in the direction of the right or left photodiode 7 (FIG. 5). If the thickness variation of the sheet of material 2 is sufficiently large (2') (FIG. 4), the transmitted light bar 4 will reach one of the two diodes 7, as indicated at 4', thus triggering a control action whereby an electric motor 9 is started and through reduction gearing 38 adjusts the folding mirror 6 (FIG. 4).

For checking purposes, the receiving section 17 preferably is constructed as a drawer unit. In other words, the complete housing 18 preferably is provided with rollers 23 (FIG. 2a) which run on rails 22 so that the housing can be pushed into the inspection apparatus and removed therefrom.

Figure 6:
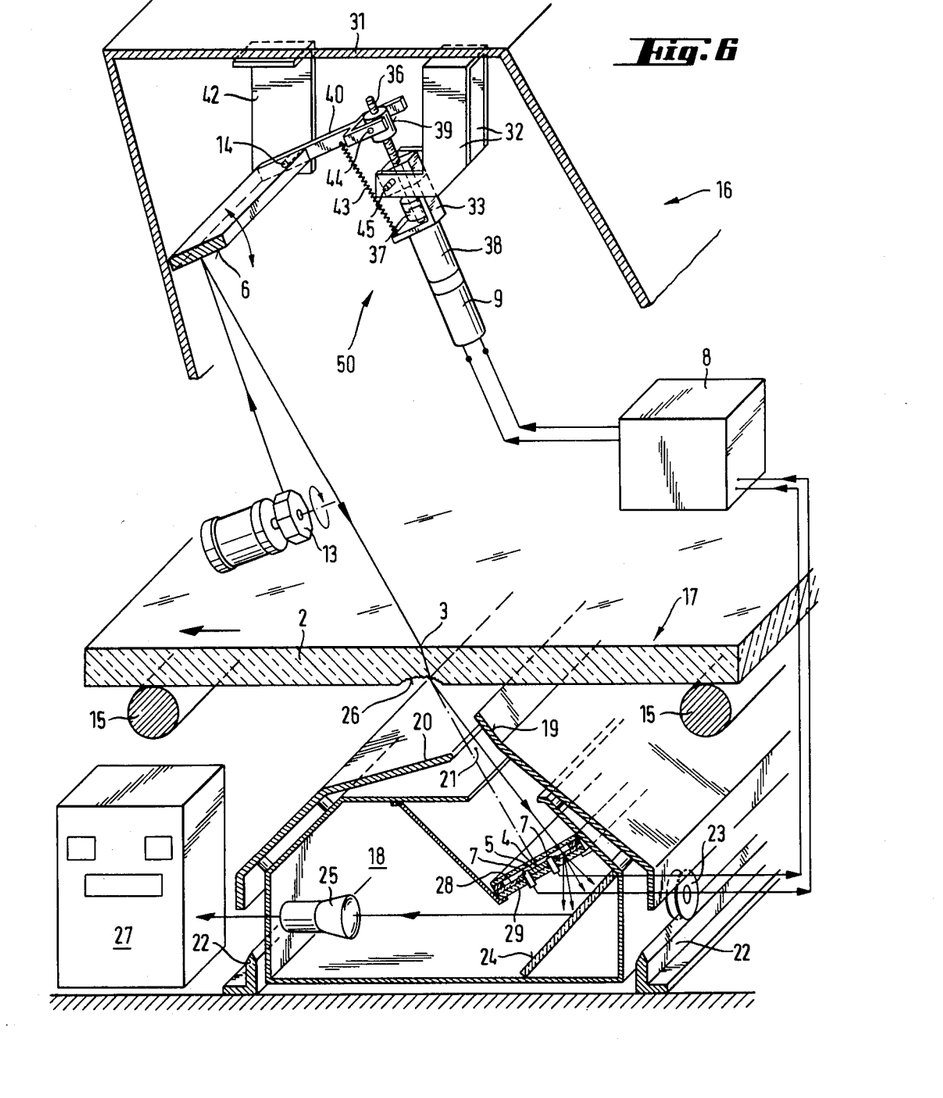
FIG. 6 represents diagrammatically the deflection of the beam due to a surface deformation.

When the continuous sheet of material 2 to be inspected contains a defect 26, as shown in FIG. 6, there occurs, in contradistinction to the initially slow displacement of the light bar 3 on the sheet of material, a sudden momentary deflection of a portion of the transmitted light bar 4 which falls onto the light-diffusing plate 1 outside the stop 5, reflected by a deflecting mirror 24 to a photomultiplier 25 that is connected to an evaluation and control station 27.

Figure 7:
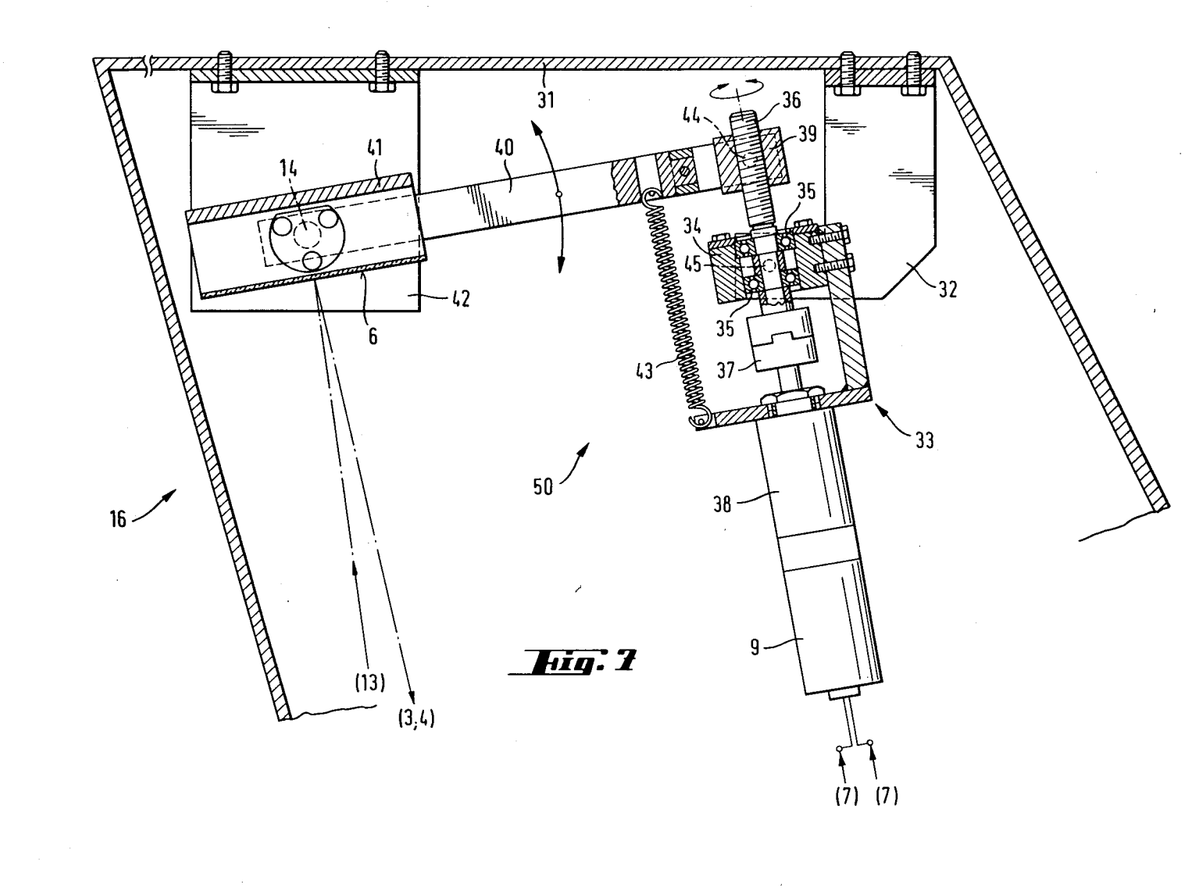
FIG. 7 is a diagrammatic, sectional view, to an enlarged scale, of the adjustment apparatus of the reflecting mirror.

Shown in detail in FIG. 7 is a preferred tracking mechanism for the folding mirror 6. To the cover plate 31 of the transmitting section 16 there is attached a two-strap bracket 32. The latter comprises two bearing pins 45 on which a mount 34 is pivotally supported. Disposed in the mount 34 are bearings 35 for a threaded stud 36. The latter is driven through a motor 9, a transmission 38 and a clutch 37.

The motor 9 and the transmission 38 are secured through an angle plate 33 to the pivotable mount 34.

When a control signal is triggered by the photodiodes, it reaches, after amplification, the electric motor 9, which thus is started and, depending on which of the photodiodes 7 triggered the control pulse, rotates in a clockwise or counterclockwise direction. The rated speed of the electric motor 9 preferably is 5,000 rpm, and the reduction ratio of the transmission 38 preferably is 7,860 to 1, so that the threaded stud 36, which preferably carries an M 12 fine thread with a 1-mm pitch, turns only at a low speed. The threaded stud 36 engages an adjustment nut 39, which is pivotably mounted at 44 on a rocking lever 40. The lever 40 engages a frame structure 41 which accommodates the folding mirror 6 and is supported on a pivot 14. The pivot 14 is disposed in a mount 42 that is secured to the cover plate 31 of the transmitting section 16.

To compensate for any backlash between the threaded stud 36 and the adjusting nut 39, an extension spring 43 preferably is secured to the rocking lever 40 in proximity to the adjusting nut 39, its other bend being hooked into the angle plate 33.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. Apparatus for the inspection of a continuous sheet of a light-transmissive material which may have defects comprising:

a light source for supplying a light beam;

first and second movable mirror means, said first movable mirror means being associated with said light source for directing a beam of light to said second movable mirror means for reflecting the light beam onto the sheet of material to be inspected;

receiver means for receiving the reflected light comprising a plurality of light-responsive transducer means and a housing including light-diffusing means;

the reflected light beam falling on an opaque area of said light-diffusing means, when the continuous sheet of material is free of defects;

at least one of said light-responsive transducer means being disposed with respect to said reflected light beam after said light-diffusing means and forming a defect-detecting transducer;

a plurality of said light-responsive transducer means being spaced relative to each other in the direction of travel of the continuous sheet of material within said opaque area of said light-diffusing means; and control means responsive to said transducer means located within said opaque area for re-positioning said second mirror means in response to gradual thickness changes of the light-transmissive material.

2. Apparatus according to claim 1, in which said control means includes tracking means for re-positioning said second mirror means, said tracking means comprising an electric motor and an extremely geared-down transmission.

3. Apparatus according to claim 1, in which said control means comprises a three-level action closed loop.

4. Apparatus according to claim 1, in which said light-diffusing means comprises an opaque sheet applied to a light-diffusing plate as a stop for blocking the reflected light beam.

5. Apparatus according to claim 4, in which the position of said stop on said light-diffusing plate is adjustable.

6. Apparatus according to claim 1, in which said second mirror means comprises a folding mirror of the optical path and said light-responsive transducer means located in said opaque area provide signals having amplitudes representing a measure for the re-positioning of the folding mirror.

7. Apparatus according to claim 1, in which said light source comprises a laser.

8. Apparatus according to claim 1, in which said first movable mirror means comprises a rotatable mirror.

9. Apparatus according to claim 1, in which said two transducers means located in said opaque area comprise two photodiodes.

* * * * *